United States Patent [19]
Riswick et al.

[11] Patent Number: 5,804,519
[45] Date of Patent: Sep. 8, 1998

[54] HOT MELT ADHESIVE COMPOSITIONS

[75] Inventors: Martin Riswick, Marlow, United Kingdom; Gary F. Raykovitz, Flemington, N.J.

[73] Assignee: National Starch and Chemical Investment Holding Corporation, Wilmington, Del.

[21] Appl. No.: 968,869

[22] Filed: Nov. 5, 1997

Related U.S. Application Data

[60] Continuation of Ser. No. 457,898, Jun. 1, 1995, abandoned, which is a division of Ser. No. 330,159, Oct. 27, 1994, abandoned.

[51] Int. Cl.⁶ .................. A61F 13/15; A61F 13/20
[52] U.S. Cl. .............. 442/392; 442/381; 442/389; 442/393; 442/417; 604/366; 604/372; 604/373
[58] Field of Search ...................... 156/327, 334; 604/366, 372, 373; 428/343–355; 442/392, 393, 381, 389, 417

[56] References Cited

U.S. PATENT DOCUMENTS

| | | | |
|---|---|---|---|
| 3,341,343 | 9/1967 | Beiswanger et al. | 106/177 |
| 3,492,372 | 1/1970 | Flanagan | 260/897 |
| 4,136,699 | 1/1979 | Collins et al. | 428/355 |
| 4,345,349 | 8/1982 | Flanagan | 412/5 |
| 4,411,954 | 10/1983 | Butch, III et al. | 428/343 |
| 4,419,494 | 12/1983 | Puletti et al. | 525/95 |
| 4,460,728 | 7/1984 | Schmidt, Jr. et al. | 524/271 |
| 4,526,577 | 7/1985 | Schmidt, Jr. et al. | 604/366 |
| 4,683,001 | 7/1987 | Floyd et al. | 106/3 |
| 4,874,804 | 10/1989 | Brady et al. | 524/100 |
| 4,895,567 | 1/1990 | Colon et al. | 604/361 |
| 5,001,179 | 3/1991 | Kauffman et al. | 524/275 |
| 5,130,196 | 7/1992 | Nishio et al. | 428/373 |
| 5,169,890 | 12/1992 | Eadara et al. | 524/271 |
| 5,331,033 | 7/1994 | Stauffer et al. | 524/275 |

FOREIGN PATENT DOCUMENTS

| | | |
|---|---|---|
| 55-172461 | 10/1981 | Japan . |
| 58-074771 A | 5/1983 | Japan . |
| 57-72035 | 11/1983 | Japan . |
| 58-189273 A | 11/1983 | Japan . |
| 2294397 | 10/1994 | United Kingdom ............ A61L 15/58 |

*Primary Examiner*—Ana Woodward
*Attorney, Agent, or Firm*—Ellen T. Dec; Lydia T. McNally

[57] ABSTRACT

A method for improving the strike through properties of hot melt adhesive compositions comprising the step of incorporating therein a nonionic fluorchemical surfactant in an amount of 0.1 to 10 parts by weight per 100 parts adhesive.

9 Claims, No Drawings

HOT MELT ADHESIVE COMPOSITIONS

This application is a continuation of application Ser. No. 08/457,898, filed Jun. 1, 1995, which is a divisional of Ser. No. 08/330,159 filed Oct. 27, 1994 both now abandoned.

BACKGROUND OF THE INVENTION

A nonwoven fabric is defined as an interlocking fiber network characterized by flexibility, porosity and integrity. The individual fibers used to compose the nonwoven fabric may be synthetic, naturally occurring, or a combination of the two. The individual fibers may be mechanically, chemically, or thermally bonded to each other. Nonwovens are used commercially for a variety of applications including insulation, packaging, household wipes, surgical drapes, medical dressings, and in disposable articles such as diapers, adult incontinent products and sanitary napkins. Tissue is a closely related material in which the individual fibers may or may not be chemically bonded to one another.

In many of the aforementioned applications it is necessary to adhere the nonwoven or tissue to another substrate or component. The second substrate may be another nonwoven, tissue, or an unrelated material. A commonly employed technique to bond the assembly together is the use of a hot melt adhesive. Hot melt adhesives allow for cost and time efficient manufacturing since there is no evaporation step necessary as is the case for water based or solvent based adhesive systems. Suitable hot melt adhesives must possess excellent adhesion to the substrates involved. For nonwoven applications they must also possess good flexibility (or hand), no staining or bleed through, suitable viscosity, set speed and open time to function on commercially available equipment and finally, acceptable thermal aging properties.

Recently a variety of nonwoven and tissue applications have been developed which require that the hot melt adhesive demonstrate the ability to transmit the liquid from the nonwoven substrate into the superabsorbent or fluff core substrates. This property, referred to as strike through, is especially important in disposable diaper, sanitary napkin and bed pad constructions where it is desired to draw the moisture away from the body and into the absorbent core as quickly as possible after the nonwoven is wetted.

SUMMARY OF THE INVENTION

It has now been discovered that the addition of a fluorochemical surfactant to conventional hot melt adhesives increases the hydrophilic character of the hot melt adhesives. When a coating of the resultant hot melt is applied between the coverstock nonwoven and the absorption pad of the disposable product, the hydrophilic character of the hot melt improves the strike through properties of the liquid as compared to conventional hot melt coatings which, more often, serve as a barrier to the liquid transmission.

While various surfactants have been added to hot melt adhesives to reduce their foaming tendencies or to improve adhesion, it was unexpected that the addition of these specific fluorochemical surfactants would not only provide acceptable adhesion levels but would also provide improved strike through without reducing the absorbency speed or capacity of the absorbing material, properties essential for the particular end use applications.

DETAILED DESCRIPTION OF THE PREFERRED EMBODIMENTS

The fluorochemical surface active agents utilized herein are nonionic in character and essentially comprise blends of $C_7$ and $C_8$ fluorinated alkyl alkoxylates and fluorinated alkyl sulfonamides. They are present in an amount of 0.1 to about 10 parts, preferably 0.5 to 5 parts, per 100 parts of the adhesive composition. Commercially available surfactants are obtained from 3M Chemical Company, as FLUORAD FC 430, FC 1802 and FC 171. They comprise approximately 86 to 89% $C_8$ fluorinated alkyl alkoxylate, 9 to 10% $C_8$ fluorinated alkyl sulfonamide, 2 to 4% $C_7$ fluorinated alkyl alkoxylate and 0.1 to 1% fluorinated alkyl sulfonamide. These materials are characterized, respectively, by Brookfield viscosities (25° C.) of 7000 cp (spindle #3 @ 6 rpm) and 150 cp (spindle #1 @ 60 rpm); specific gravity @ 25° C. of about 1.1, 1.4 and 1.4.

The fluorochemical surfactant may be added to virtually any hot melt adhesive used in disposable construction applications including, but not limited to, those hot melt adhesive compositions based on ethylene/vinyl acetate copolymers, isotactic or atactic polypropylene, styrene-butadiene, styrene-isoprene, or styrene-ethylene-butylene A-B-A or A-B-A-B block copolymers or mixtures thereof. In addition to the base polymer, these hot melt adhesive compositions generally contain tackifiers, oils and/or waxes as well as conventional additives including stabilizers, anti-oxidants, pigments and the like. Typical of such formulations are those described in U.S. Pat. Nos. 4,460,728 issued Jul. 17, 1984 to R. C. Schmidt, Jr. et al.; 3,492,372 issued Jan. 27, 1970 to T. P. Flanagan; 4,411,954 issued Dec. 6, 1983 to P. P. Puletti et al.; 4,136,699 issued Jan. 30, 1979 to J. A. Collins et al.

In more detail, the fluorochemical surfactant may be added to adhesives based on rubbery block copolymers. These polymers include the block or multi-block copolymers having the general configuration: A-B-A or A-B-A-B-A-B- wherein the polymer blocks A are non-elastomeric polymer blocks which, as homopolymers have glass transition temperatures above 20° C., while the elastomeric polymer blocks B are butadiene or isoprene or butadiene isoprene which is partially or substantially hydrogenated. Further, they may be linear or branched. Typical branched structures contain an elastomeric portion with at least three branches which can radiate out from a central hub or can be otherwise coupled together.

The non-elastomeric blocks which make up 14 to 50% by weight of the block copolymer may comprise homopolymers or copolymers of vinyl monomers such as vinyl arenes, vinyl pyridines, vinyl halides and vinyl carboxylates, as well as acrylic monomers such as acrylonitrile, methacrylonitrile, esters of acrylic acids, etc. Monovinyl aromatic hydrocarbons include particularly those of the benzene series such as styrene, vinyl toluene, vinyl xylene, ethyl vinyl benzene as well as dicyclic monovinyl compounds such as vinyl naphthalene and the like. Other non-elastomeric polymer blocks may be derived from alpha olefins, alkylene oxides, acetals, urethanes, etc. Styrene is preferred.

The elastomeric block component making up the remainder of the copolymer is isoprene or butadiene which may or may not be hydrogenated as taught, for example, in U.S. Pat. No. 3,700,633. This hydrogenation may be either partial or substantially complete. Selected conditions may be employed for example to hydrogenate the elastomeric block while not so modifying the vinyl arene polymer blocks. Other conditions may be chosen to hydrogenate substantially uniformly along the polymer chain, both the elastomeric and non-elastomeric blocks thereof being hydrogenated to practically the same extent, which may be either partial or substantially complete.

Typical of the rubbery block copolymers useful herein are the polystyrene-polybutadiene-polystyrene, polystyrenepolyisoprene-polystyrene and e.g., polystyrene-poly-(ethylenebutylene)-polystyrene and polystyrene-poly-(ethylenepropylene)-polystyrene. These copolymers may be prepared using methods taught, for example, in U.S. Pat. Nos. 3,239,478; 3,427,269; 3,700,633; 3,753,936; and 3,932,327. Alternatively, they may be obtained from Shell Chemical Co. under the trademarks Kraton 1101, 1102, 1107, 1650, 1652 and 1657; from Enichem under the Europrene Sol-T tradenames; and from Firestone under the tradename Stereon 840A.

Other adhesive compositions may be prepared according to the invention using, as a base polymer, amorphous polyolefins or blends thereof. Amorphous polyolefins are made by the stereospecific polymerization of polypropylene. Polymerization occurs in the presence of a catalyst comprising a coordination complex of a transition metal halide with an organometallic compound. The solid amorphous polypropylene has a softening point of about 150° and a viscosity at 190° C. of 1,000 to 4,500 cps. Suitable commercial products include Eastmans P 1010. Copolymers of amorphous polypropylene and ethylene (APE), butene (APB) and hexene (APH) are suitable as a base polymer, as are terpolymrs of propylene, butene and ethylene (APBF). Commercial examples of APE include Rextac 2315 from Rexene, of APB including Rextac 2730 from Rexene and APBE include Vestoplast 750 and 708 from Hüls.

Ethylene containing polymers are also commonly used for disposable applications and can be improved by the addition thereto of the fluorchemicals in accordance with the teachings of the invention. Thus ethlylene is polymerized with 15 to 45% by weight of such copolymerizable monomers as vinyl acetate, N-butyl acrylate, propylene, methyl acrylate, methyl acrylic acid, acrylic acid, metallocene catalyzed ethylene based polymers and the like as well as mixtures thereof.

Blends of any of the above base materials, such as blends of ethylene vinyl acetate and atactic polypropylene may also be used to prepare the hot melt adhesive composition. In all cases, the adhesives are formulated with tackifying resins, plasticizers, waxes and/or other conventional additives in varying amounts as are known to those skilled in the art.

The tackifying resins useful in the adhesive compositions can be hydrocarbon resins, synthetic polyterpenes, rosin esters, natural terpenes, and the like. More particularly, and depending upon the particular base polymer, the useful tackifying resins may include any compatible resins or mixtures thereof such as (1) natural and modified rosins such, for example, as gum rosin, wood rosin, talloil rosin, distilled rosin, hydrogenated rosin, dimerized rosin, and polymerized rosin; (2) glycerol and pentaerythritol esters of natural and modified rosins, such, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natured terpenes, e.g., styrene/terpene and alpha methyl styrene/terpene; (4) polyterpene resins having a softening point, as determined by ASTM method E28-58T, of from about 80° to 150° C.; the latter polyterpene resins generally resulting from the polymerization of terpene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol; (6) aliphatic petroleum hydrocarbon resins having a Ball and Ring softening point of from about 70° to 135° C.; the latter resins resulting from the polymerization of monomers consisting of primarily of olefins and diolefins; also included are the hydrogenated aliphatic petroleum hydrocarbon resins; (7) aromatic petroleum hydrocarbon resins and the hydrogenated derivatives thereof; and (8) alicyclic petroleum hydrocarbon resins and the hydrogenated derivatives thereof. Mixtures of two or more of the above described tackifying resins may be required for some formulations.

Various plasticizing or extending oils are also present in the composition in amounts of 5% to about 30%, preferably 5 to 25%, by weight in order to provide wetting action and/or viscosity control. Even higher levels may be used in cases where block copolymer containing hydrogenated mid-block are employed as the adhesive base polymer. The above broadly includes not only the usual plasticizing oils but also contemplates the use of olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less than 15% by weight of the oil). Alternatively, the oil may be totally non-aromatic. The oligomers may be polypropylenes, polybutenes, hydrogenated polyisoprene, hydrogenated polybutadiene, or the like having average molecular weights between about 350 and about 10,000. Vegetable and animal oils include glyceryl esters of the usual fatty acids and polymerization products thereof.

Various petroleum derived waxes may also be used in amounts less than about 15% by weight of the composition in order to impart fluidity in the molten condition of the adhesive and flexibility to the set adhesive, and to serve as a wetting agent for bonding cellulosic fibers. The term "petroleum derived wax" includes both paraffin and microcrystalline waxes having melting points within the range of 130° to 225° F. as well as synthetic waxes such as low molecular weight polyethylene or Fisher-Tropsch waxes.

An antioxidant or stabilizer may also be included in the adhesive compositions described herein in amounts of up to about 3% by weight. Among the applicable antioxidants or stabilizers are high molecular weight hindered phenols and multifunctional phenols such as sulfur and phosphorous-containing phenols. Representative hindered phenols include: 1,3,5-trimethyl 2,4,6-tris (3,5-di-tert-butyl-4-hydroxy-benzyl)benzene; pentaerythritol tetrakis-3(3,5-di-tert-butyl-4-hydroxyphenyl)-propionate; n-octadecyl-3,5-di-tert-butyl-4-hydroxyphenol)-propionate; 4,4'-methylenebis (2,6-tert-butylphenol); 4,4'-thiobis (6-tert-butyl-o-cresol); 2,6-di-tertbutylphenol; 6-(4-hydroxyphenoxy)-2,4-bis(n-octyl-thio)-1,3,5-triazine; di-n-octadecyl 3,5-di-tert-butyl-4-hydroxy-benzyl-phosphonate; 2n-octylthio)-ethyl 3,5-di-tert-butyl-4hydroxy-benzoate and sorbitol hexa[3-(3,5-ditert-butyl-4-hydroxyphenyl)-propionate].

Other additives conventionally used in hot melt adhesives to satisfy different properties and meet specific application requirements also may be added to the adhesive composition of this invention. Such additives include fillers, pigments, flow modifiers, dyestuffs, etc., which may be incorporated in minor or larger amounts into the adhesive formulation, depending on the purpose.

These hot melt adhesives may be prepared using techniques known in the art. Typically, the adhesive compositions are prepared by blending the components in the melt at a temperature of about 100° to 200° C. until a homogeneous blend is obtained, approximately two hours. Various methods of blending are known and any method that produces a homogeneous blend is satisfactory. The resulting adhesives are characterized in that they have a viscosity of 20,000 cP or less at the application temperature of 350° F. (177° C.) or less. The viscosity as used herein is a Brookfield viscosity measured using a Brookfield viscometer model No. DV-II with spindle no. 27 at 10 rpm.

The resulting adhesives of the present invention are characterized by their ability to provide a durable bond to a nonwoven or tissue article and otherwise meet the unique requirements of the application (including flexibility, non-staining, and machinable viscosity). The adhesives described herein also possess exceptional thermal stability which distinguishes them from other moisture sensitive technologies. Further, their hydrophilic natures facilitated ready transmission of the fluid throughout the construction.

The adhesive product can be applied to a substrate such as a nonwoven article or tissue by a variety of methods including coating or spraying in an amount sufficient to cause the article to adhere to another substrate such as tissue, nonwoven, or an unrelated material such as a low density polyolefin or other conventionally employed substrates.

The following examples illustrate the production of suitable hot melt adhesives or binders as well as the use thereof in a variety of applications. In the examples, all parts are by weight and all temperatures in degree Celsius unless otherwise noted. Test procedures used herein are as follows:

TEST PROCEDURES

180° T Peel Testing Procedure

The samples are prepared as follows. A glue line was extruded onto polyethylene (25 micron) at approximately 300° to 325° F. with a line speed of 100 FPM to form a glue line approximately 0.5 mm wide with a coating weight of approximately 0.03 to 0.05 gr/linear meter. A polypropylene nonwoven substrate was immediately bonded to the glue bead with bonding pressure of approximately 60 psi. Samples were then cut parallel to adhesive lines, leaving at least ⅛" on each side of the exterior adhesive lines. The samples were conditioned overnight at 70° F./50% RH constant temperature and humidity. Testing was also done on tissue to tissue samples.

Instron Testing

The ends of each sample were taped, then placed in jaws, with the adhesive coated nonwoven in the stationary jaw. The sample was pulled at 12 in/min crosshead speed, 2 in/min chart speed in 180° T peel mode and the average peel value recorded in grams or pounds for each product tested. If there was bond failure, the type of failure was recorded instead of peel value.

Contact Angle Test

As a drop of liquid meets a solid surface, it assumes a distinctive shape. The shape and length of time that it holds onto its shape are determined by three interfacial tension forces: the force of the solid surface, the surface tension of the liquid and the force at the solid/liquid interface. The contact angle (θ) is a measured value relative to the combined vector forces according to the formula:

$$y_L \cos \theta = y_S - y_{SL}$$

where $y_L$ is the interfacial tension of the liquid/air boundary, $y_S$ is the interfacial tension of the solid/air boundary, $y_{SL}$ is the interfacial tension of the solid/liquid boundary, and θ is the angle of the liquid drop.

The goniometer has a microsyringe for dispersing accurate droplet sizes and a camera for photographing the angle of the liquid drop as it meets the surface of the solid. The contact angle is measured as the angle between the substrate and the tangent of the liquid drop (at the interface).

The lower the angle, the more effective the coating is in transmitting the liquid through the adhesive layer.

EXAMPLE 1

The following rubber based hot melt adhesive was prepared and various amounts of FC 1802 (a fluorchemical surfactant from 3M) were added thereto.

|  | Parts |  |
| --- | --- | --- |
| Stereon 840A | 23 | Firestone |
| Mineral Oil | 18 | Witco |
| Unitac R98 Lite | 59 | Union Camp |
| A.O. | 0.5 | Ciba Giegy |

Contact angle measurements of the adhesives were made initially, and after 48 hours at 350° F. (177° C.) to determine thermal stability of the FC 1802 in system. The results are shown in Table I.

TABLE I

|  | CONTROL | 2.5% | 5.0% | 10.0% | 20.9% |
| --- | --- | --- | --- | --- | --- |
| INITIAL STABILITY | 77° | 62° | 27° | 27° | <17 |
| AFTER STABILITY | — | 72° | 62° | 46° | 28° |

The results indicate that after exposure to elevated temperatures for extended periods of time, the presence of the surfactant still presented a noticeably beneficial effect on the coating.

EXAMPLE 2

This example was performed to show the specificity of the fluorchemical surfactant in their effect on the hot melt adhesives. In this case other conventional surfactants were added to the adhesive described in Example 1.

TABLE II

|  | 5 PARTS PLURONIC F68 | 5 PARTS IGAPAL CO-890 | 0.3 PARTS SILWET L 7607 |
| --- | --- | --- | --- |
| INITIAL | 80° | 70° | 82° |
| AFTER 48 HOURS AT 350° F. | 74° | 74° | 74° |

Pluronic F68-ethylene oxide propylene oxide block polymer-BASF
Igapal CO 890-nonylphenol ethoxylate-Rhone Poulenc
Silwet L 7607-silicone-OSI The results presented in Table II show that the surfactants tested were not as effective as FC 1802 before or after stability.

EXAMPLE 3

The following example illustrates the use of various levels of the fluorchemical surfactants in the following conventional atactic polypropylene based hot melt adhesive:

TABLE III

| Indopol H100 | 23 | polyisobutylene (Amoco) |
|---|---|---|
| Vestoplast 750 | 38 | terpolymer of polypropylene/polybutene/polyethylene (Hüls) |
| Eastotac H100 | 37 | partially hydrogenated $C_5$ (Eastman) |
| A.O. | 0.5 | hindered phenol |

| | CONTROL | 0.1%-FC 171 | 0.5%-FC 171 | 1.0%-FC 171 |
|---|---|---|---|---|
| INITIAL | 100° | 89° | 78° | 58° |
| 24 HOURS AT 350° F. | 98° | 91° | 70° | 68° |

EXAMPLE 4

The adhesive described in Example 3 was also tested for its bond strength using the 180° peel test. Products were applied at 130° C. at coating weights of 0.03 gr/linear meter and 0.05 gr/linear meter (pattern was a multiline using a Meltex Coater).

TABLE IV

| GRAM/ 3 LINES | STANDARD APAO HM | | +0.2% SURFACTANT (FC 171) | | +0.5% SURFACTANT (FC 171) | |
|---|---|---|---|---|---|---|
| COATING WEIGHT* | 0.03 | 0.05 | 0.03 | 0.05 | 0.03 | 0.05 |
| INITIAL | 104 | 215 | 125 | 230 | 90 | 168 |
| AFTER 24 HOURS | 100 | 254 | 130 | 270 | 70 | 164 |
| AFTER 1 MONTH | 130 | 180 | 175 | 360 | 115 | 250 |

*Grams/Linear Meter

The test results presented in Table IV show bond values adequate at 0.2, 0.5, and 1.0% levels at 24 hours and after 1 month of aging at ambient conditions.

EXAMPLE 5

Another series of tests on the adhesive of Example 3 were performed to determine whether the fluorchemical surfactant and the effect thereof would remain in the adhesive after soaking in water at 35° C. for 1½ hours.

TABLE V

| | FC 171 0.1% | FC 171 0.3% | CONTROL |
|---|---|---|---|
| INITIAL | 68° | 79° | 100° |
| AFTER SOAKING | 75° | 67° | — |

The results show that the flurochemical surfactant remain effective after repeated dosing of the diaper with synthetic urine.

EXAMPLE 6

In addition to the testing described above, nonwoven substrates coated with 5 mg per square inch of the various adhesives were subjected to standard testing to determine the degree of penetration/absorption of synthetic urine through the coated substrate when the substrate was placed on an inclined surface. The amount of time, in seconds, required for all the liquid to pass through the coated substrate was noted. The results indicate that nonwovens coated with the fluorchemical surfactant containing adhesive exhibited rapid absorption of at least two doses (5 ml each) of the liquid as compared with the same nonwoven substrate which had been coated with standard adhesives. The results are shown in Table VI.

TABLE VI

| | FIRST DOSE | SECOND DOSE | THIRD DOSE |
|---|---|---|---|
| APAO BASED CONTROL | 3 | 22 | >25 |
| APAO BASED +0.5% FC-430 | 3 | 12 | 21 |
| RUBBER BASED CONTROL | 9 | 22 | 21 |
| RUBBER BASED +0.5% FC-430 | 5 | 9 | 22 |

These results clearly demonstrate the suitability of the adhesives for nonwoven and other disposable applications. Similar results would be expected using fluorchemical containing adhesives prepared from other polymer bases and/or adhesives containing compatible formulating materials.

In summary, the results show that these hot melt adhesives may be successfully used to form nonwoven disposable product as described hereinabove. It will be apparent that various changes and modifications may be made in the embodiments of the invention described above, without departing from the scope of the invention, as defined in the appended claims, and it is intended therefore, that all matter contained in the foregoing description shall be interpreted as illustrative only and not limitative of the invention.

We claim:

1. A process for bonding tissue or nonwoven substrate to similar or dissimilar substrates in the construction of a disposable absorbent product comprising the steps of applying to at least one substrate a molten hot melt adhesive composition and bonding said substrates together, said hot melt adhesive containing 0.1 to 10 parts by weight of a fluorochemical surfactant per 100 parts of the adhesive.

2. The process of claim 1 wherein the fluorochemical surfactant in the adhesive comprises a blend of $C_7$ and $C_8$ fluorinated alkyl alkoxylates and fluorinated $C_7$ and $C_8$ alkyl sulfonamides.

3. The process of claim 2 wherein the fluorochemical surfactant comprises 9 to 10% $C_8$ fluorinated alkyl sulfonamide, 2 to 4% $C_7$ fluorinated alkyl alkoxylate, 0.1 to 1% $C_7$ fluorinated alkyl sulfonamide and sufficient $C_7$ fluorinated alkyl alkoxylate to total 100% by weight.

4. The process of claim 1 wherein the fluorochemical surfactant in the adhesive is present in an amount of 0.5 to 5 parts per 100 parts of the adhesive.

5. The process of claim 1 wherein the hot melt adhesive is based on a polymer selected from the group consisting of ethylene/vinyl acetate copolymers, isotactic polypropylene, atactic polypropylene, styrene-isoprene A-B-A or A-B-A-B block copolymers, sytrene-butadiene A-B-A or A-B-A-B block copolymers, styrene-ethylene-butylene A-B-A or A-B-A-B block copolymers, styrene-ethylene-propylene A-B-A or A-B-A-B block copolymers and mixtures thereof.

6. A disposable absorbent product produced by the process of claim 1.

7. The disposable absorbent product of claim 6 comprising a disposable diaper.

8. The disposable absorbent product of claim 6 comprising a multi-ply sanitary napkin.

9. A disposable absorbent product containing incorporated therein at least one nonwoven substrate containing superabsorbent particulate polymers, wherein the disposable absorbent product is produced by the process of claim 1.

* * * * *